United States Patent [19]

Wright

[11] 4,431,669

[45] Feb. 14, 1984

[54] CYCLOPROPYL SUBSTITUTED POLYENES

[75] Inventor: John J. Wright, Cedar Grove, N.J.

[73] Assignee: Schering Corporation, Kenilworth, N.J.

[21] Appl. No.: 450,624

[22] Filed: Dec. 17, 1982

[51] Int. Cl.$^3$ .................. C07C 61/18; C07C 69/74; A61K 31/19; A61K 31/215

[52] U.S. Cl. .................. 424/317; 424/305; 424/320; 560/118; 562/500; 564/188

[58] Field of Search .................. 560/118; 562/500; 564/188; 424/305, 317, 320

[56] References Cited

U.S. PATENT DOCUMENTS

| | | | |
|---|---|---|---|
| 3,950,418 | 4/1976 | Bollag et al. | 424/320 |
| 4,126,698 | 11/1978 | Gander et al. | 424/305 |
| 4,190,594 | 2/1980 | Gander et al. | 424/305 |
| 4,304,787 | 12/1981 | Gander et al. | 424/305 |

FOREIGN PATENT DOCUMENTS 762344 2/1971 Belgium .................. 424/317

OTHER PUBLICATIONS

*Journal of Medicinal Chemistry*, vol. 25, No. 11, pp. 1269–1277 (1982), Pawson et al., "Retinoids at the Threshold: Their Biological Significance and Therapeutic Potential".

*Primary Examiner*—Natalie Trousof
*Assistant Examiner*—Patricia M. Scott
*Attorney, Agent, or Firm*—Gerald S. Rosen; Bruce M. Eisen

[57] ABSTRACT

There is disclosed certain cyclopropyl substituted polyenes useful for treating dermatoses such as acne, psoriasis and epithelial cancers.

16 Claims, No Drawings

CYCLOPROPYL SUBSTITUTED POLYENES

SUMMARY OF THE INVENTION

This invention relates to certain cyclopropyl substituted polyene compounds which are useful in treating dermatoses in warm-blooded animals, methods of their preparation, pharmaceutical compositions containing them as the active agent and methods of treating dermatoses with the compounds.

More particularly, this invention is concerned with compounds represented by the formula

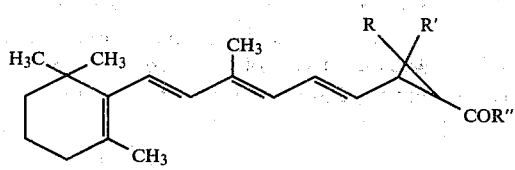

wherein

R and R' are independently selected from hydrogen and lower alkyl;

R" is selected from hydroxy, lower alkoxy or —NHR''' wherein R''' is hydrogen or lower alkyl;

and the pharmaceutically acceptable salts thereof.

As used herein "lower alkyl" means straight and branched chain alkyl groups which contain from 1 to 6 carbon atoms, e.g. methyl, ethyl, propyl, butyl, tertiary butyl, isopropyl and the like. "Pharmaceutically acceptable salts" means salts wherein the acidic hydrogen in the carboxylic acid derivatives of this invention, e.g. wherein R" is hydroxy, is replaced by a cation, e.g. an alkali metal such as sodium or potassium. The salts are prepared by procedures well known in the art.

The preferred compounds of this invention are:
4-E-[2,3-trans-isopropylidene-7-methyl-9-(2,6,6-trimethyl-cyclohexen-1-yl)]nona-4,6,8-trienoic acid; and 4-Z-[2,3-trans-isopropylidene-7-methyl-9-(2,6,6-trimethyl-cyclohexen-1-yl)]nona-4,6,8-trienoic acid.

DETAILED DESCRIPTION OF THE INVENTION

The compounds of this invention are useful in the topical and systemic treatment of dermatoses such as acne and psoriasis and other keratinization disorders which are accompanied by an increased or pathologically altered cornification in warm-blooded animals, including humans. The compounds of this invention can be used for topical and systemic therapy of benign pre-malignant lesions as well as for the systemic and topical prophylaxis of these conditions.

The anti-acne activity of the compounds of this invention was measured in an animal model for measuring comedolytic activity in which retinoic acid, a compound known to be an effective anti-acne agent, is known to be effective. In this model the compounds of this invention were found to have activity and potency similar to retinoic acid. For example, when 4-E-[2,3-trans-isopropylidene-7-methyl-9-(2,6,6-trimethyl-cyclohexen-1-yl)]nona-4,6,8-trienoic acid was applied topically it was effective at a daily dose of 0.02 mgm, as was retinoic acid.

In the foregoing test, the test compound was applied topically to a circumscribed area of skin on the posterior dorsal aspect of the mouse. Twenty-four hours following the last application, portions of the skin from treated and untreated areas were excised, fixed in formalin and processed for histological assessment.

Psoriasis is characterized by increased epidermipoiesis associated with a high mitotic rate, rapid cell turn-over and altered keratinization. The psoriatic epidermis can be normalized by slowing down cell growth through inhibiting mitosis.

The anti-psoriatic activity of the compounds of this invention was measured in an animal model for measuring the effect of the test compounds on mitotic rate in croton oil-stimulated epidermis. In this model the compounds of this invention were found to be active. For example, when 4-E-[2,3-trans-isopropylidene-7-methyl-9-(2,6,6-trimethyl-cyclohexen-1-yl]nona-4,6,8-trienoic acid was applied topically it was effective at a daily dose of 0.1 mgm.

In the foregoing test which is a procedure modified from Belman et al, Cancer Research 32, 450-454 (1972), the test compound was applied topically to a circumscribed area of skin on the posterior dorsal aspect of the mouse with a croton oil solution. Controls were treated only with croton oil. Twenty-four hours later the rats were injected (i.p.) with colcemid in saline to block cells entering metaphase. Four hours later skin from the treated areas were excised and processed for histology. The results indicated the test compounds effectively reduced mitosis.

The compounds of this invention may be administered enterally, parenterally or topically. The dosages will vary according to the judgment of the attending clinician taking into account the mode of administration, the condition being treated and the requirements of the patient. For oral administration, from about 5 mg to about 200 mg of the compounds daily in one or more dosages are contemplated. A preferred oral dosage form is capsules containing from about 10 mg to about 100 mg of the active ingredients. For topical administration, preferred dosage forms are solutions containing the active ingredient in from 0.01% by weight to about 0.3% by weight, preferably from about 0.02% by weight to about 0.1% by weight, and lotions, gels, ointments and creams containing from about 0.5% by weight to about 5% by weight, preferably from about 0.1% by weight to about 2.0% by weight of the active ingredients.

The compounds of this invention can be used as medicaments in the form of pharmaceutical preparations which contain them in association with a compatible carrier material.

Pharmaceutical preparations for systemic administration can be prepared, for example, by adding a compound of this invention as the active ingredient to pharmaceutically acceptable, non-toxic, inert, solid or liquid carriers which are usual in such preparations. The pharmaceutical preparations can be administered enterally, parenterally or topically. Suitable preparations for enteral administration are, for example, tablets, capsules, dragees, syrups, suspension, solutions and suppositories. Suitable pharmaceutical preparations for parenteral administration are infusion solutions.

The pharmaceutical preparations can contain in addition to the active compounds of this invention, pharmaceutically acceptable inert or pharmacodynamically active additives. Tablets or granules, for example, can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor improving additives and pharmaceutically acceptable substances commonly used as preservatives, stabilizers, moisture retainers or emulsifiers, salts for varying the osmotic pressure, buffers and other pharmaceutically acceptable additives can also be present in the pharmaceutical preparations.

The aforementioned pharmaceutically acceptable carrier materials and diluents are well known to the pharmaceutical compounding art and can be organic or inorganic substances such as water, gelatin, lactose, magnesium stearate, talc, gum arabic, polyalkyleneglycols and the like. It is, of course, a prerequisite that all adjuvants used in the preparation of the pharmaceutical preparations are non-toxic and pharmaceutically acceptable.

For topical administration, the compounds of this invention are expediently made up in the form of salves, gels, tinctures, creams, solutions, lotions, sprays, suspensions transdermal devices and the like. Ointments, creams and lotions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

A conventional pharmaceutically acceptable antioxidant, e.g. tocopherol, N-methyl-$\gamma$-tocopheramine, butylated hydroxyanisole or butylated hydroxytoluene can also be incorporated into the pharmaceutical preparations containing the compounds of this invention.

The compounds of this invention can occur as isomers at the newly formed olefinic linkage which can be separated into the 4E and 4Z compounds or isomerized to the all E compound by conventional means. They are prepared as follows:

Reacting a phosphonium salt represented by the formula

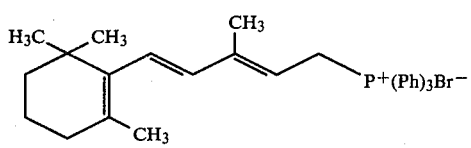

with a base to form the corresponding phosphorane, then reacting the phosphorane in situ with a cyclopropane aldelyde represented by the formula

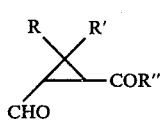

wherein R and R' are as hereinabove defined and R" is lower alkoxy to yield a cyclopropyl substituted polyene represented by the formula

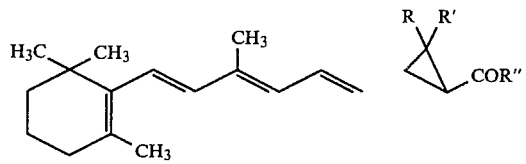

Method A

The reaction is conducted in the cold, about $-20°$ C. to about $0°$ C., in an appropriate organic solvent such as dichlormethane in the presence of an alkali metal salt of a lower alkoxide. The reaction is completed in about one hour. Because of the solvent used, the product is predominately the 2,3-trans-isomer of the formula

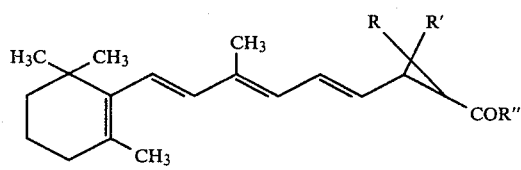

Method B

A suspensiodn of the phosphonium salt depicted above, in an appropriate non-isomerizing solvent such as ether, is treated with a hexane solution or an organolithium reagent such as m-butyllithium at $-30°$ C. The cyclopropyl aldehyde reactant is added and the solution is allowed to warm to $0°$ C. over one hour.

The phosphonium and cyclopropyl aldehyde are known compounds or can be made from known compounds by methods known in the art.

The products resulting from either Method A or Method B can be recovered by chromatography and the esters hydrolyzed to the corresponding acids. The acids can be converted into amides where R" is NHR'" by methods known in the art, e.g. as in peptide synthesis wherein an activated ester such as succinyloxyester is reacted with an amine, or a coupling reaction using dicyclohexyldicarbodiimide as the coupling agent is employed.

The acids can be converted into their pharmaceutically acceptable salts by conventional means known in the art.

Use of the cis cyclopropane aldehydro esters in a Wittig reaction using Method B provides the corresponding 2,3-cis cyclopropane derivative of the formula

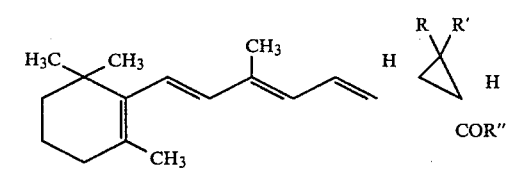

wherein R and R' are as hereinabove defined and R" is lower alkoxy.

The following examples illustrate the preparations of the compounds and compositions of this invention.

EXAMPLE 1

4-E and 4-Z-[2,3-trans-isopropylidene-7-methyl-9-(2,6,6-trimethyl-cyclohexene-1-yl)]nona-4,6,8-trienoic acid 15 grams of a solution of [beta ionyl-idineethyl]triphenylphosphonium bromide and 3.9 grams of ethyl trans-2,2-dimethyl-3-formyl-cyclopropane carboxylate in dichlormethane (150 ml) was cooled to −20° C. A solution of sodium methoxide (1.9 g) in methanol (30 ml) was added over 15 minutes. The reddish-orange solution was stirred at 0° for 1 hour, diluted with hexane-ethyl acetate (7:3, 300 ml) and washed with water and dried. Removal of the solvent gave an orange solid which was extracted with ether. The ether extracts were evaporated to give orange solids which were subjected to high pressure liquid chromatography in 1.5% ethylacetate-hexane.

Two fractions were obtained which were separately subjected to hydrolysis of the ester to give the corresponding carboxylic acid.

Thus, 1.76 g of the fraction first eluted was treated with 54 ml of a 1:1 mixture of DMSO-50% KOH under argon at room temperature for 4 hours. The reddish mixture was poured into a cold 1 N HC solution (60 ml) and acidified with 5 N HCl to pH 1. The resulting mixture was extracted with ether and the ether extracts were washed with water, followed by brine, and dried. Evaporation of the solvent gave the 4-Z-isomer as a foam. Data was obtained on the ethyl ester: $^1$H NMR (CDCl$_3$) $\delta$1.0 (6H, s, 2C—CH$_3$; 1.16 (3H, s, C—CH$_3$); 1.25 (3H, t, J=7Hz, CH$_2$—CH$_3$); 1.26 (3H, s, C—CH$_3$; 1.68 (3H, s, =C—CH$_3$); 1.90 (3H, s, =C—CH$_3$); 2.14 (1H, dd, J=8.5, 5.0 Hz, H-3); 4.15 (2H, q, J=7 Hz, CH$_2$CH$_3$); 5.46 (1H, dd, J=8.5, 15.0 Hz, H-4); 5.8–6.3 (3H, m, H-6, H-8 and H-9); 7.60 (1H, dd, J=15.0, 11.0 Hz, H-5): UV (MeOH) $\lambda$max 302 nm ($\epsilon$=1.65×10$^4$).

Similar treatment of the second fraction to elute (0.9 g) gave the 4-E-acid as a foam. Data was obtained on the ethyl ester: $^1$H NMR (CDCl$_3$) $\delta$1.00 (6H, s, 2C—CH$_3$); 1.16 (3H, s, C—CH$_3$); 1.24 (3H, t, J=7 Hz, CH$_2$CH$_3$); 1.25 (3H, s, C—CH$_3$); 1.66 (3H, s, =C—CH$_3$); 1.9 (3H, s, =C—CH$_3$); 2.39 (1H, dd, J=9.0, 5.0 Hz, H-3); 4.15 (2H, q, J=7 Hz, CH$_2$CH$_3$); 5.20 (1H, t, J=9.0, 9.0 Hz, H-4); 6.2–6.5 (4H, m, H-5, H-6, H-8 and H-9. UV (MeOH $\lambda$max 300 nm ($\epsilon$=1.94×10$^4$).

In the following compositions "active ingredient" means the preferred compounds of this invention or equivalent amounts of any of the compounds within the scope of this invention.

EXAMPLE 2

Cream

|  | mg/g |
|---|---|
| Active ingredient | 10.0 |
| Cetyl alcohol | 40.0 |
| Stearyl alcohol | 40.0 |
| Isopropyl myristate | 100.0 |
| Polyoxyethylene (2) monostearyl ether (Brij 72) | 10.0 |
| Polyoxyethylene (20) monostearyl ether (Brij 78) | 25.0 |
| Propylene glycol | 100.0 |
| Benzyl alcohol | 10.0 |
| Purified water q.s. ad | 1.0 g |

Method of Manufacture

Melt together and heat to about 70° C. cetyl alcohol, stearyl alcohol, Brij 72, Brij 78 and isopropyl myristate. Add the propylene glycol to water in a separate container, heat to 70° C., and dissolve in this aqueous phase the benzyl alcohol. Dissolve or suspend the active ingredient in the aqueous phase while stirring. Add the aqueous phase to the oil phase with agitation. Continue stirring while cooling the cream to room temperature.

EXAMPLE 3

Gel

|  | mg/g |
|---|---|
| Active ingredient | 10.0 |
| Propylene glycol | 50.0 |
| Hydroxypropylcellulose | 25.0 |
| Ethyl alcohol q.s. ad | 1.0 g |

Method of Manufacture

Disperse or dissolve in the active ingredient in alcohol with agitation. Add the propylene glycol and then the hydroxypropylcellulose, maintaining agitation until the hydroxypropylcellulose is evenly dispersed. Cool the resulting gel to allow for completion of hydration.

EXAMPLE 4

Lotion

|  | mg/g |
|---|---|
| Active ingredient | 10.0 |
| Ethyl alcohol | 450.0 |
| Polyethylene glycol 400 | 350.0 |
| Hydroxypropylcellulose | 5.0 |
| Propylene glycol q.s. ad | 1.0 g |

Method of Manufacture

Dissolve or disperse the active ingredient in the solvent mixture of ethyl alcohol, polyethylene glycol 400 and propylene glycol with agitation. Then add hydroxypropyl-cellulose maintaining agitation, until the hydroxypropyl-cellulose is evenly dispersed.

EXAMPLE 5

Ointment

|  | mg/g |
|---|---|
| Active ingredient | 10.0 |
| Mineral Oil | 50.0 |
| White Petrolatum q.s. ad | 1.0 g |

Method of Manufacture

Melt the petrolatum with heat and stirring. Slurry the active ingredient in mineral oil and add to the melted petrolatum. Continue stirring, while cooling the ointment to room temperature.

I claim:

1. A compound represented by the formula

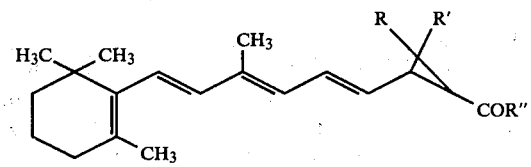

wherein
R and R' are independently selected from hydrogen and lower alkyl;
R" is selected from hydroxy, lower alkoxy or —NHR'" wherein R'" is hydrogen or lower alkyl;
and the pharmaceutically acceptable salts thereof.

2. A compound of claim 1 which is the 4E isomer.
3. A compound of claim 1 which is the 4Z isomer.
4. A compound of claim 1 which is the 2,3-cis-isomer.
5. A compound of claim 1 which is the 2,3-trans-isomer.
6. A compound of claim 2 which is 4-E-[2,3-trans-isopropylidene-7-methyl-9-(2,6,6-trimethyl-cyclohexen-1-yl)]nona-4,6,8-trienoic acid.
7. A compound of claim 3 which is 4-Z-[2,3-trans-isopropylidene-7-methyl-9-(2,6,6-trimethyl-cyclohexen-1-yl)]nona-4,6,8-trienoic acid.
8. A pharmaceutical composition for the treatment of dermatoses comprising an anti-dermatoses effective amount of a compound of claim 1, together with a non-toxic pharmaceutically acceptable carrier.
9. A composition of claim 8 adapted for topical administration.
10. The composition of claim 8 wherein said compound is 4-Z-[2,3-trans-isopropylidene-7-methyl-9-(2,6,6-trimethylcyclohexen-1-yl)]nona-4,6,8-trienoic acid.
11. The composition of claim 8 wherein said compound is 4-E-[2,3-trans-isopropylidene-7-methyl-9-(2,6,6-trimethyl-cyclohexen-1-yl)]nona-4,6,8-trienoic acid.
12. A method of treating dermatoses comprising administering to a warm-blooded animal having a dermatosis disease, an anti-dermatoses amount of a compound of claim 1, together with a non-toxic pharmaceutically acceptable carrier.
13. A method of claim 12, wherein the dermatosis is acne.
14. A method of claim 12, wherein the dermatosis is psoriasis.
15. A method of claim 12, wherein the compound is 4-E-[2,3-trans-isopropylidene-7-methyl-9-(2,6,6-trimethyl-cyclohexen-1yl)]nona-4,6,8-trienoic acid.
16. A method of claim 12, wherein the compound is 4-Z-[2,3-trans-isopropylidene-7-methyl-9-(2,6,6-trimethylcyclohexen-1-yl)]nona-4,6,8-trienoic acid.

* * * * *